United States Patent [19]
Lees

[11] Patent Number: 6,087,328
[45] Date of Patent: Jul. 11, 2000

[54] COUPLING OF UNMODIFIED PROTEINS TO HALOACYL OR DIHALOACYL DERIVATIZED POLYSACCHARIDES FOR THE PREPARATION OF PROTEIN-POLYSACCHARIDE VACCINES

[75] Inventor: Andrew Lees, Silver Spring, Md.

[73] Assignee: Henry M. Jackson Foundation for the Advancement of Military Medicine, Rockville, Md.

[21] Appl. No.: 09/064,827

[22] Filed: Apr. 23, 1998

Related U.S. Application Data

[60] Provisional application No. 60/042,379, Apr. 24, 1997.

[51] Int. Cl.$^7$ .................................................. A61K 38/16
[52] U.S. Cl. .............................................. 514/8; 530/350
[58] Field of Search ................................ 530/350; 514/8

[56] References Cited

U.S. PATENT DOCUMENTS

| | | | |
|---|---|---|---|
| 3,278,392 | 10/1966 | Patchornik et al. | 435/179 |
| 3,816,254 | 6/1974 | Chibata et al. | 435/179 |
| 4,185,090 | 1/1980 | McIntire | 424/197.11 |
| 4,328,311 | 5/1982 | Rowley et al. | 435/188 |
| 4,695,624 | 9/1987 | Marburg et al. | 424/197.11 |
| 4,830,852 | 5/1989 | Marburg et al. | 424/85.8 |
| 5,204,098 | 4/1993 | Szu et al. | 424/194.1 |
| 5,445,817 | 8/1995 | Schneerson et al. | 424/194.1 |
| 5,565,204 | 10/1996 | Kuo et al. | 424/244.1 |
| 5,651,971 | 7/1997 | Lees | 424/194.1 |
| 5,693,326 | 12/1997 | Lees | 424/194.1 |

FOREIGN PATENT DOCUMENTS

| | | |
|---|---|---|
| 9508348 | 3/1995 | WIPO . |
| WO 96/29094 | 9/1996 | WIPO . |

OTHER PUBLICATIONS

Landsteiner, The Specificity of Serological Reactions (Revised Ed.), Harvard University Press, Cambridge, MA, 1945, only pp. 51 and 156–158 supplied.

Lees, A. et al., "Enhanced Immungencity of Protein–Dextran Conjugates: I. Rapid Stimulation of Enhanced Antibody Response to Poorly Immunogenic Molecules," Vaccine, vol. 12, No. 13, pp. 1160–1166, (1994).

Inman J.K., "Syntheses of Macromolecular Immunomodulators and Conjugates Employing Haloacetyl Reagents," Annals of the N.Y. Academy of Science, vol. 685, pp. 347–350, (1993).

Beuvery, E.C., et al., "Characteristics of Two Type of Meningococcal Group C Polysaccharide Conjugates Using Tetanus Toxiod as Carrier Protein," Develop. Biol. Standard, vol. 65, pp. 197–204, (1986).

Ibrahim et al., "Proportion of Protein A Bindable Molecules in Human IgM and IgA Antibodies to Seven Antigens," Mocrobial Pathogenesis, 15(3), 159–168 (Sep., 1993).

Lees et al., "Activation of Soluble Polysaccharides with 1–Cyano–4–dimethylaminopyridinum Tetrafluoroborate for Use in Protein–Polysaccharide Conjugate Vaccines and Immunological Reagents," Vaccine, 14(3), 190–198 (Feb., 1996).

Erlanger, "The Preparation of Antigenic Hapten–Carrier Conjugates: A Survey," Ch. 4 in Method in Enzmology, vol. 70, Part A, Vunakis and Langone (eds.), Academic Press, New York, NY, 1980, pp. 85–104.

Peters et al., "Chemical Cross–Linking: Reagents and Problems in Studies of Membrane Structure," Ann. Reviews in Biochemistry, 46, 523–551 (1977).

Primary Examiner—L. Eric Crane
Attorney, Agent, or Firm—Finnegan, Henderson, Farabow, Garrett & Dunner, L.L.P.

[57] ABSTRACT

A method for preparing a conjugate, and preferably a protein-polysaccharide conjugate, includes functionalizing a first moiety (e.g., a polysaccharide) with one or more pendant haloacyl groups. Thereafter, the functionalized first moiety is reacted with a second moiety, preferably an unmodified protein or a protein to which no thiol groups have been added, to form a covalently linked conjugate. Various different haloacyl reagents can be used in the invention. For example, the haloacyl reagent can be an active ester, an anhydride, a haloacyl chloride, or a haloacyl acid. Specific haloacyl reagents that can be used in the process of the invention include N-succinimidyl-2,3-dibromopropionate and N-succinimidyl iodoacetate. The invention further relates to the conjugates produced by the method of the invention. These conjugates can be used as immunogens or vaccines. Furthermnore, the invention also relates to a method of inducing an immune response in a subject by administering a vaccine made by the method according to the invention.

18 Claims, 4 Drawing Sheets

R–NH–(CH$_2$)$_y$–$\overset{\overset{\displaystyle O}{\|}}{C}$–O–R$_1$ wherein y = 1 to 10

R–O–R, or wherein y = 1 to 10

R–Cl, or wherein y = 1 to 10

R-OH, or wherein y = 1 to 10

R is

X is Cl, Br, I

COUPLING OF UNMODIFIED PROTEINS TO HALOACYL OR DIHALOACYL DERIVATIZED POLYSACCHARIDES FOR THE PREPARATION OF PROTEIN-POLYSACCHARIDE VACCINES

RELATED APPLICATION DATA

This application claims priority benefits based on U.S. Provisional Patent Application No. 60/042,379, filed Apr. 24, 1997, which application is entirely incorporated herein by reference.

BACKGROUND OF THE INVENTION

Vaccines have been very effective in protecting people from a wide variety of diseases, whether caused by viruses, bacteria, or fungi. The ability of vaccines to induce specific is protection against such a wide range of pathogenic organisms results from their ability to stimulate specific humoral antibody responses, as well as cell-mediated responses. This invention relates to a process for preparing such vaccines, and particularly to a process for making conjugates that are used in vaccines and immunogens. The invention further relates to the vaccines and immunogens produced from the conjugates made according to the invention, as well as to the use of these products.

It is often very desirable to induce immune responses against polysaccharides. For example, antibodies against a bacterial capsular polysaccharide can provide protection against that bacterium. Many polysaccharides, however, are poorly immunogenic, particularly in infants and young children. Furthermore, in both children and adults, there is usually no booster effect with repeated polysaccharide immunizations, and the principal antibody class is IgM. These features are all characteristic of so called "T cell independent" ("TI") antigens.

In many cases, the immunogenicity of polysaccharides can be enhanced by covalently linking proteins or T cell epitope-containing peptides or haptens to the polysaccharide. Certain other components, such as lipids, fatty acids, lipopolysaccharides, and lipoproteins, also are known to enhance the immunogenicity of the polysaccharide. As described in the "dual conjugate" patent application of Mond and Lees, conjugation of a protein to a polysaccharide can enhance the immune response to the protein as well as to the polysaceharide. See U.S. Pat. No. 5,585,100; U.S. patent application. Ser. No. 08/444,727 (filed May 19, 1995); and U.S. patent application Ser. No. 08/468,060 (filed Jun. 6, 1995). This patent and these patent applications each are entirely incorporated herein by reference. This effect also is described in A. Lees, et al., "Enhanced Inimunogenicity of Protein-Dextran Conjugates: I. Rapid Stimulation of Enhanced Antibody Responses to Poorly Immunogenic Molecules," *Vaccine*, Vol. 12, No. 13 (1994), pp. 1160–1166. This article is entirely incorporated herein by reference. In view of this potential for improving the immune response against polysaccharides, there is a need in the art for methods to covalently link proteins or other moieties to polysaecharides.

Ideally, the process of covalently linking proteins (or other moieties) to a polysaccharide should be done in a way to maintain antigenicity of both the polysaccharide and protein (or other) components and to minimize damage to necessary epitopes of each component. Furthermore, the linkage should be stable. Therefore, there is a need for a mild and gentle means for stably coupling proteins, peptides, haptens, or other moieties to polysaccharides.

Two main methods for coupling molecules together are used. In the first method, the means for coupling entails the crosslinking of a protein (or peptide or other moiety) directly to a polysaccharide (or some other moiety). Sometimes, however, a spacer molecule is needed between the coupled moieties, either to facilitate the chemical process and/or to enhance the immune response to the protein and/or the polysaccharide. In either method, it usually is necessary to activate or functionalize the polysaccharide before crosslinking occurs. Some methods of activating or functionalizing polysaccharides are described in W. E. Dick, et al., "Glycoconjugates of Bacterial Carbohydrate Antigens: A Survey and Consideration of Design and Preparation Factors," *Conjugate Vaccines* (Eds. Cruse, et al.), Karger, Basel, 1989, Vol. 10, pp. 48–114. This excerpt is entirely incorporated herein by reference. Additional activation methods are described in R. W. Ellis, et al. (Editors), *Development and Clinical Uses of Haemophilus B Conjugate Vaccines*, Marcel Dekker, New York (1994), which book is entirely incorporated herein by reference.

One preferred method for activating polysaccharides is described in the "CDAP" (1-cyano-4-dimethylaminopyridine tetrafluoroborate) patent applications of Lees, U.S. patent application Ser. No. 08/124,491 (filed Sep. 22, 1993, now abandoned); U.S. Pat. No. 5,651,971; U.S. Pat. No. 5,693,326; and U.S. patent application Ser. No. 08/482,666 (filed Jun. 7, 1995). These U.S. patents and patent applications each are entirely incorporated herein by reference. The use of CDAP also is described in Lees, et al., "Activation of Soluble Polysaccharides with 1-Cyano-4-Dimethylamino Pyridinium Tetrafluoroborate For Use in Protein-Polysaccharide Conjugate Vaccines and Immunological Reagents," *Vaccine*, Vol. 14, No. 3 (1996), pp. 190–198. This article also is entirely incorporated herein by reference.

Underivatized (or urnmodified) proteins can be conjugated to polysaccharides containing amine or hydrazide spacers using crosslinkers, such as gluteraldehyde or carboduimide. These methods, however, are prone to cause aggregation and homopolymerization, are difficult to control, and are likely to cause significant modification of the protein. These side effects are generally undesirable.

Instead of covalently linking proteins and polysaceharides via a spacer, a protein can be coupled to a polysaecharide with a spacer using heteroligation chemistry. In this procedure, the protein and polysaccharide components each are functionalized with chemical groups, and then the group (s) on the protein react selectively with the functional group(s) on the polysaccharide.

A common heteroligation method for linking proteins and polysaccharides via a spacer is through the use of a thioether linkage. See, for example, S. Marburg et al., *Journal of the American Chemical Society*, Vol. 108 (1986), beginning at page 5282, and U.S. Pat. No. 4,695,624, issued Sep. 22, 1987, which documents each are entirely incorporated herein by reference. Typically in this scheme, the polysaccharide is derivatized with an electrophilic group such as an α-haloacid, e.g., an iodoacetyl group, the protein is functionalized with thiol groups, and the two are combined. The thiol group attacks the α-carbon on the haloacid group and forms a thio-ether linkage.

Another known heteroligation method includes the formation of disulfides, as described in U.S. Pat. No. 5,204,098 to S. C. Szu et al., dated Apr. 20, 1993 (which patent is entirely incorporated herein by reference). In this method, the protein is derivatized with thiols and the polysaccharide with an exchangeable disulfide (e.g., a dithiopyridyl). Thiols on the protein undergo a disulfide exchange and form a conjugate with the polysaccharide.

A drawback to these heteroligation methods is the necessity for functionalizing the protein, which can involve multiple steps. The protein must be reacted with the chemical label, separated from the reaction products, and usually further concentrated. These steps can be costly and can result in the loss of protein material. Furthermore, unless care is taken, the protein thiols can oxidize, potentially causing homopolymerization and decreased conjugate yields. Additionally, not all the available functional groups on the protein participate in the crosslinking process, necessitating capping of these groups, thereby introducing additional, possibly deleterious epitopes. In the disulfide method described above, the S—S bond is susceptible to cleavage.

Furthermore, during heteroligation, it is known that α-haloacids are not perfectly selective for thiols and can react with other nucleophiles found in proteins, such as the side chains found on arginine, histidine, lysine, and methionine. The α-amine terminus, tyrosine, serine, glutamic acid, aspartic acid, and threonine can also react (see Wilchek et al., "Haloacetyl Derivatives," *Methods in Enzymology*, Vol. 46 (1977), beginning at page 153, which article is entirely incorporated herein by reference). Thus, in preparing conjugates where a thio-ether linkage is desired, care must be taken to avoid side reactions involving these other groups (see Hermanson, *Bioconjugate Techniques*, 1996 Academic Press, which book is entirely incorporated herein by reference).

For certain situations, however, these side reactions have proven useful. For example, haloacids have been found to be useful in the carboxymethylation of proteins (see F. R. N. Gurd, "Carboxymethylation," *Methods of Enzymology*, Vol. 11 (1967), pp. 532–541, which article is entirely incorporated herein by reference) and in affinity labeling of proteins (see Wilchek, et al., supra.). The use of iodoacetyl labeled peptides to cyclize peptides via properly positioned methionine, lysine, arginine, or histidines also has been described (see S. J. Wood, et al., "Novel Cyclization Chemistry Especially Suited for Biologically Derived, Unprotected Peptides," *International Journal of Peptide and Protein Research*, Vol. 39 (1992), pp. 533–539, which article is entirely incorporated herein by reference).

Many of these useful haloacyl reactions require that the haloacyl group be properly positioned in order for the reaction to be successful. Indeed, this is the basis of the affinity labeling described by Wilehek et al. Similarly, in Wood's process, it is essential that the iodoacetyl group be near the reactive amino acid for peptide cyclization to occur in good yield.

For the carboxymethylation process described by Gurd, high concentrations of the haloacyl reagent are required. Furthermore, the use of only a low molecular weight reagent is described (iodoacetic acid). Applicant has found that haloacyl functionalized polysaccharides are readily reacted with low molecular weight amines at room temperature and near neutral pH. In general, it is much more difficult to react high molecular weight macromolecules as compared to low molecular weight compounds.

Despite the various coupling and activation methods and reactions described in the various documents mentioned above, there is an on-going need in the art for improved methods for coupling biologically relevant molecules to one another to produce vaccines. This invention seeks to provide an improved coupling method for producing conjugates for vaccines and immunogens. As described in this application, a polyfunctional macromolecule, such as a protein, may react with haloacyl functionalized polysaccharides under reasonably mild conditions (e.g., moderate alkalinity) to effect a stable covalent linkage of the two molecules.

SUMMARY OF THE INVENTION

This invention relates to a method for preparing conjugates, and preferably, protein-polysaccharide conjugates. In this method, a first moiety (e.g., a polysaccharide) is functionalized with one or more pendant haloacyl groups. This functionalized first moiety reacts with a second moiety (e.g., a protein) to form a covalently linked conjugate (e.g., a protein-polysaccharide conjugate).

In preferred embodiments of the invention, the second moiety is unmodified (e.g., an unmodified protein, such as unmodified tetanus toxoid protein) or it has not had thiol groups added to it (e.g., a protein not functionalized or derivatized with thiol groups).

Various different polysaccharides can be used as the first moiety in the method of the invention, such as Pneumococcal type 14 polysaccharide ("Pn-14"), Vi antigen, and *Neisseria meningiditis* polysaccharide type C ("Neisseria PsC").

To produce the functionalized first moiety material in the process of the invention, the first moiety material is reacted with a haloacyl containing reagent. Various different haloacyl reagents can be used without departing from the invention. For example, the haloacyl reagent can be a haloacyl active ester or an α,β dihaloacyl active ester reagent. Additionally, the haloacyl reagent can be a haloacyl anhydride or an α,β dihaloacyl anhydride. The reagent also can be a haloacyl chloride or an α,β dihaloacyl chloride, as well as a haloacyl acid or an α,β dihaloacyl acid. Examples of specific reagents that can be used in the process of the invention include N-succinimidyl-2, 3-dibromopropionate (an α,β dihaloacyl active ester reagent) and N-succinimidyl iodoacetate (a haloacyl active ester reagent). A preferred subclass of haloacyl reagents include haloacetyl reagents.

The invention further relates to the conjugates produced by the method of the invention. These conjugates can be used as immunogens or vaccines in a further aspect of the invention. In these instances, the conjugate produced by the method of the invention can be combined with a pharmaceutically acceptable carrier or delivery vehicle.

Furthermore, the invention also relates to a method of inducing an immune response in a subject by administering a vaccine made by the method according to the invention.

BRIEF DESCRIPTION OF THE DRAWINGS

The advantageous aspects of the invention will be more fully understood and appreciated when considered in conjunction with the following detailed description and the attached figures, wherein.

DETAILED DESCRIPTION OF THE INVENTION

The invention relates to an improved method for producing conjugates that can be used for vaccines or immunogens.

The conjugates are immunogenic in subjects to which they are administered, thereby protecting the subject from diseases and ailments caused by various organisms (bacterial, fungal, or viral organisms). To produce the conjugates according to the invention, a first moiety is functionalized with at least one pendant haloacyl group and then reacted with a second moiety. The haloacyl group can be a monohaloacyl group or a dihaloacyl group, and the halogen can be, for example, chlorine, bromine, or iodine. Haloacetyl groups are preferred as one subclass of the haloacyl reagents for use in the process of the invention.

This patent application demonstrates that first moiety molecules (e.g., polysaccharides) that have been functionalized with one or more haloacyl groups can be reacted with underivatized or unfunctionalized second moieties (e.g., proteins where no thiol groups have been added) to prepare conjugates. Such conjugates are suitable for use as vaccines and immunogens. The process of the invention also can be used to produce various immunological reagents, such as biotinyled polysaccharides.

The term "first moiety," as used in this application, includes polysaccharides, oligosaccharides, and other carbohydrates. Specific examples include dextran, carboxylated dextran (such as carboxymethyl dextran), the polysaccharides of biologically relevant bacteria, such as *Neisseria meningiditis* polysaccharide type C, Pneumnococcal polysaccharides (such as Pn14, Pn6, Pn19, and Pn23), *Haemophilus influenzae* ("PRP") polysaecharide, and PRP oligosaccharide, as well as sucrose, lipopolysaecharide, and lipooligosaccharide. Furthermore, in this application, the term "second moiety" includes materials to be covalently linked to the first moiety, including proteins, peptides, haptens, lipoproteins, and the like. Specific examples include bovine serum albumin ("B SA"), tetanus toxoid, diptheria toxoid, pertussis toxoid, Rib protein, intimin, gD protein, LHRH peptide, CFA/I consensus peptide (see F. J. Cassels, et al., *Journal of Industrial Microbiology*, 1996 Annual Meeting for the Society of Industrial Microbiology), lipoOspA, lipoD, PamCys, and monophosphorolipid A. Although this patent application may refer to "polysaecharides" or "proteins" when generally describing the invention, those skilled in the art will recognize that other first and second moieties, such as those described above, can be used without departing from the invention.

The process according to the invention differs from the processes disclosed in the various documents described in the background portion of this application. For example, conditions are used in the reaction procedure of the invention which are generally undesirable when attempting to selectively form thio-ether bonds. In the process of the invention, the pH can be alkaline (e.g., pH greater than 8), the temperatures can be somewhat elevated, and the concentrations of the components to be coupled can be relatively high. In fact, unlike processes for forming thio-ether bonds, it has been found that increasing the temperature significantly increases the yield of the conjugate product in the process of the invention. In one embodiment of the invention, the coupling reaction takes place at a temperature ranging from about 15–60° C., with about 20–50° C. being preferred.

Several advantages are realized in using the process of the invention. For example, the process of the invention allows for direct coupling of second moiety molecules to haloacyl functionalized first moiety molecules under relatively mild coupling conditions. The extent of the coupling reaction in the process of the invention can be easily monitored via high performance liquid chromatography ("HPLC") using standard techniques. Perhaps most importantly, when using the process of the invention, there is no need to functionalize the second moiety (e.g., with thiol groups) in order for conjugation to occur. These factors can reduce the cost of preparing the conjugate and can help preserve important epitopes, which can enhance the immune response. Furthermore, in the process of the invention, the second moiety is modified only if it is conjugated to the first moiety. This lack of modification of the unconjugated second moiety enables one to recover and reuse free (unreacted) second moiety components, if desired. This can be important, for instance, when the second moiety is a protein, because the protein is often the most valuable component in the conjugation reaction procedure.

The haloacyl group is stable such that in many instances the derivatized (i.e., activated) first moiety can be lyophilized and stored for later use. This feature further enhances the usefulness of the procedure according to the invention. Additionally, because all or essentially all of the reactive sites on the polysaccharide (e.g., the amine sites) are functionalized in the process of the invention, interchain and intrachain crosslinking of the polysaccharide are avoided when bifunctional reagents (e.g., N-succinimidyl-2,3-dibromopropionate, "SDBP") are used.

Many methods are available for preparing haloacyl derivatives of polysaccharides. Some suitable methods are described, for example, in Hermanson, supra. A typical protocol is to functionalize the polysaccharide with amines (or hydrazides) (e.g., with CDAP and hexanediamine (or adipic dihydrazide), as described in Lees, et al., *Vaccine*, Vol. 14, No. 3 (1996), pp. 190–198), followed by reaction with a haloacyl reagent, such as the active ester of a haloacyl (e.g., N-succinimidyl iodoacetate, "SIA"). Polysaccharide amines or hydrazides also can be reacted with acid anhydrides or acylchlorides of haloacyl reagents. Carboduimide or uronium salts can be used to couple haloacyl acids to amine or hydrazide derivatized polysaccharides. Alternatively, polysaccharide hydroxyls can be directly labeled using a haloacyl chloride. When the polysaccharide is derivatized such that a haloacyl group is attached to it, the haloacyl group is said to be a "pendant haloacyl group."

Figure 1A:
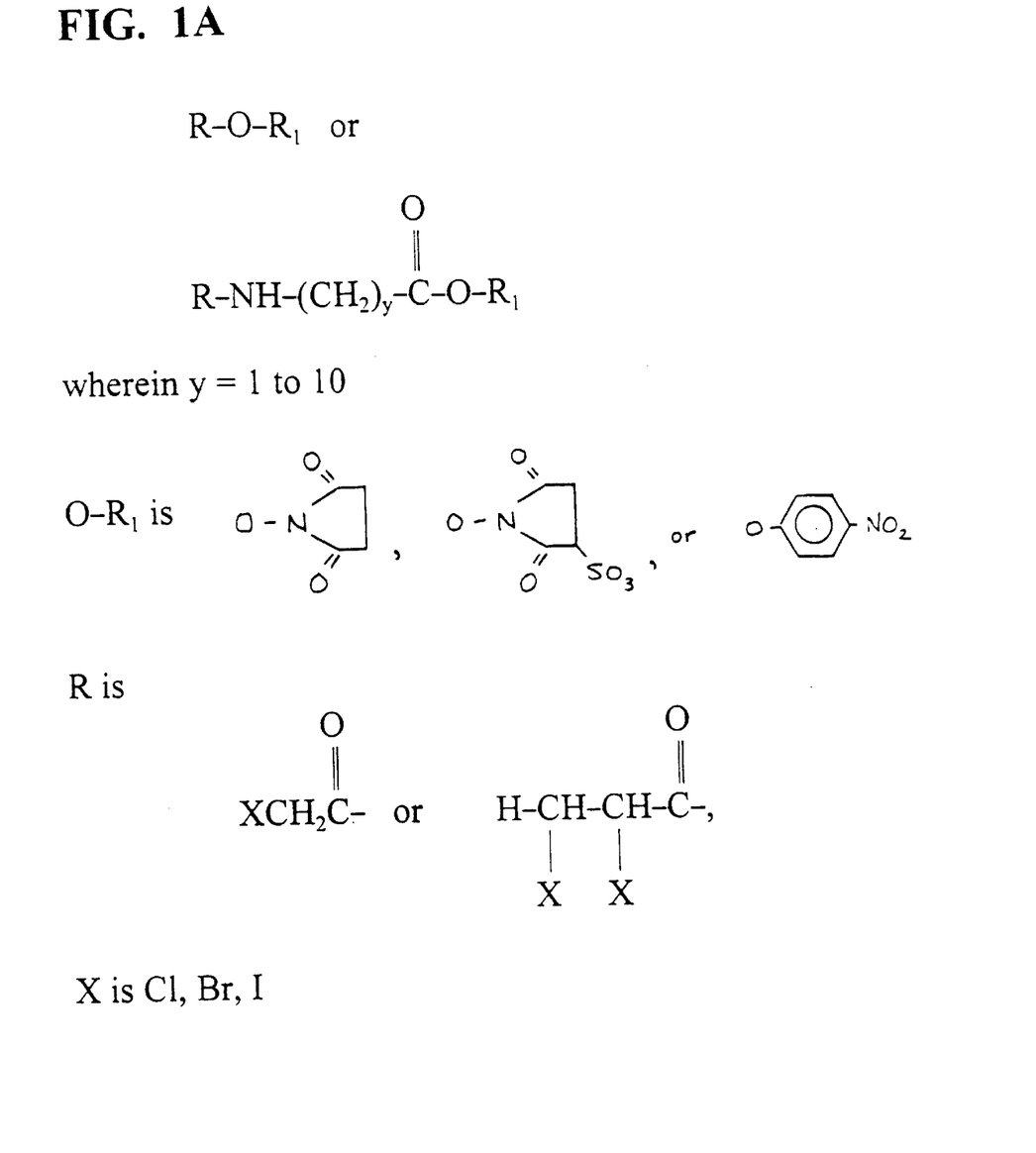
FIG. 1A illustrates haloacyl active ester reagents that can be used in the method according to the invention.
Figure 1B:
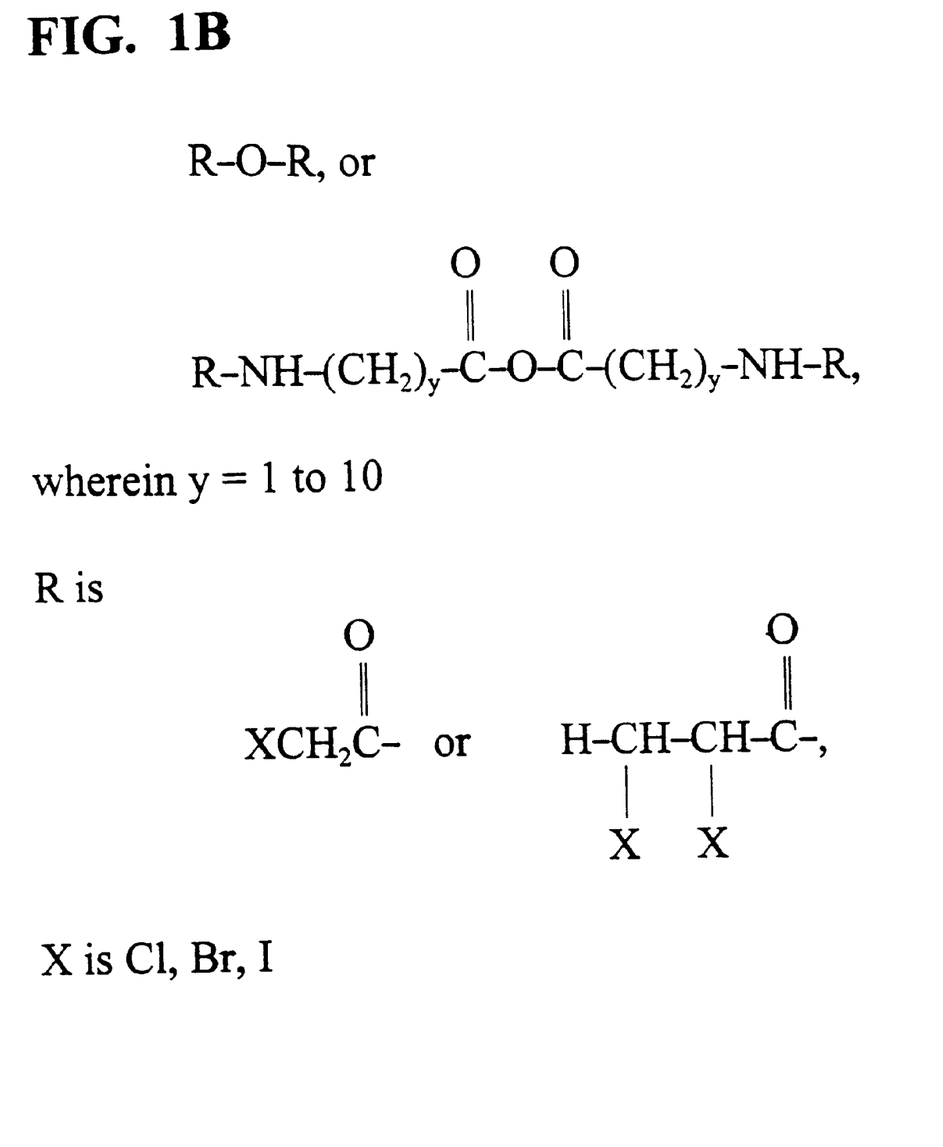
FIG. 1B illustrates haloacyl anhydride reagents that can be used in the method according to the invention.
Figure 1C:
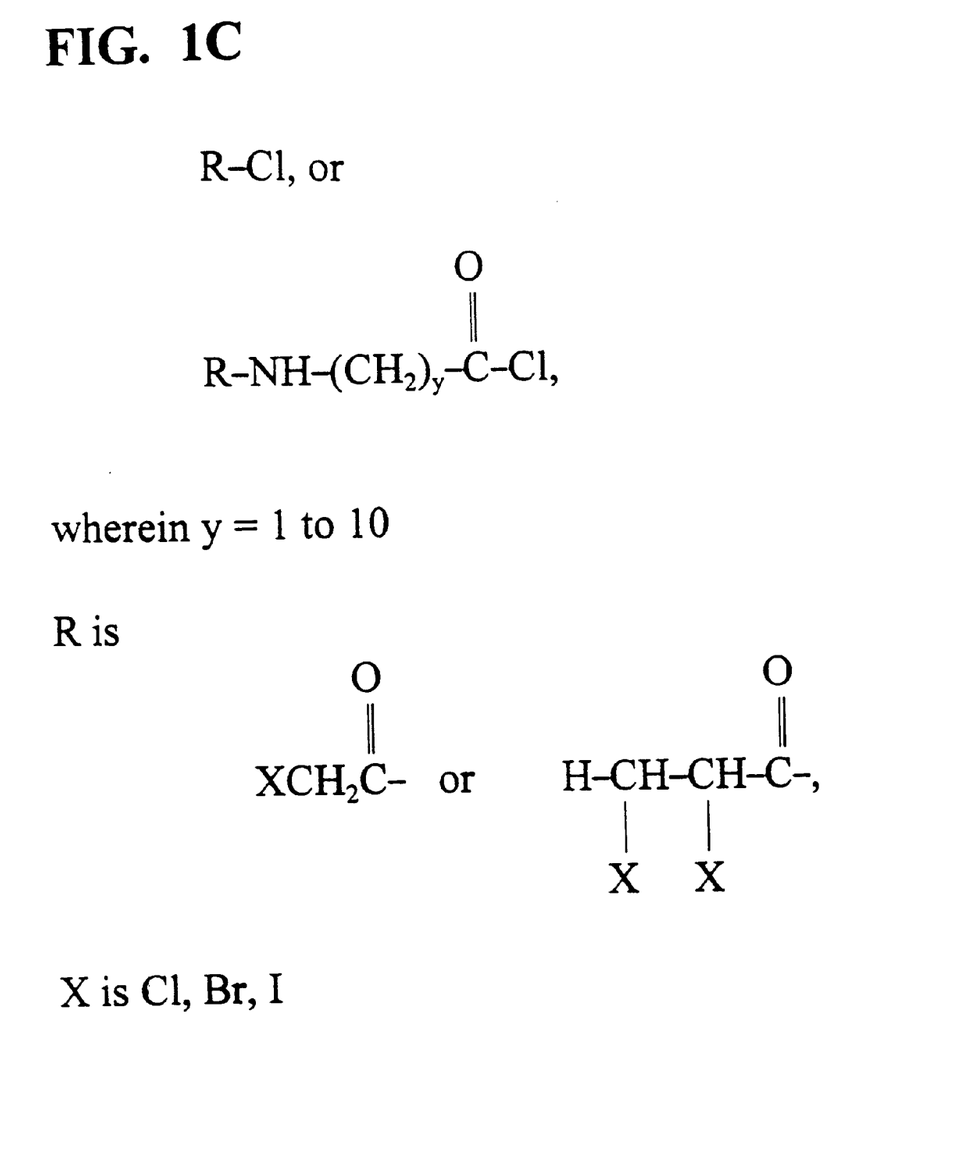
FIG. 1C illustrates haloacyl chloride reagents that can be used in the method according to the invention.
Figure 1D:
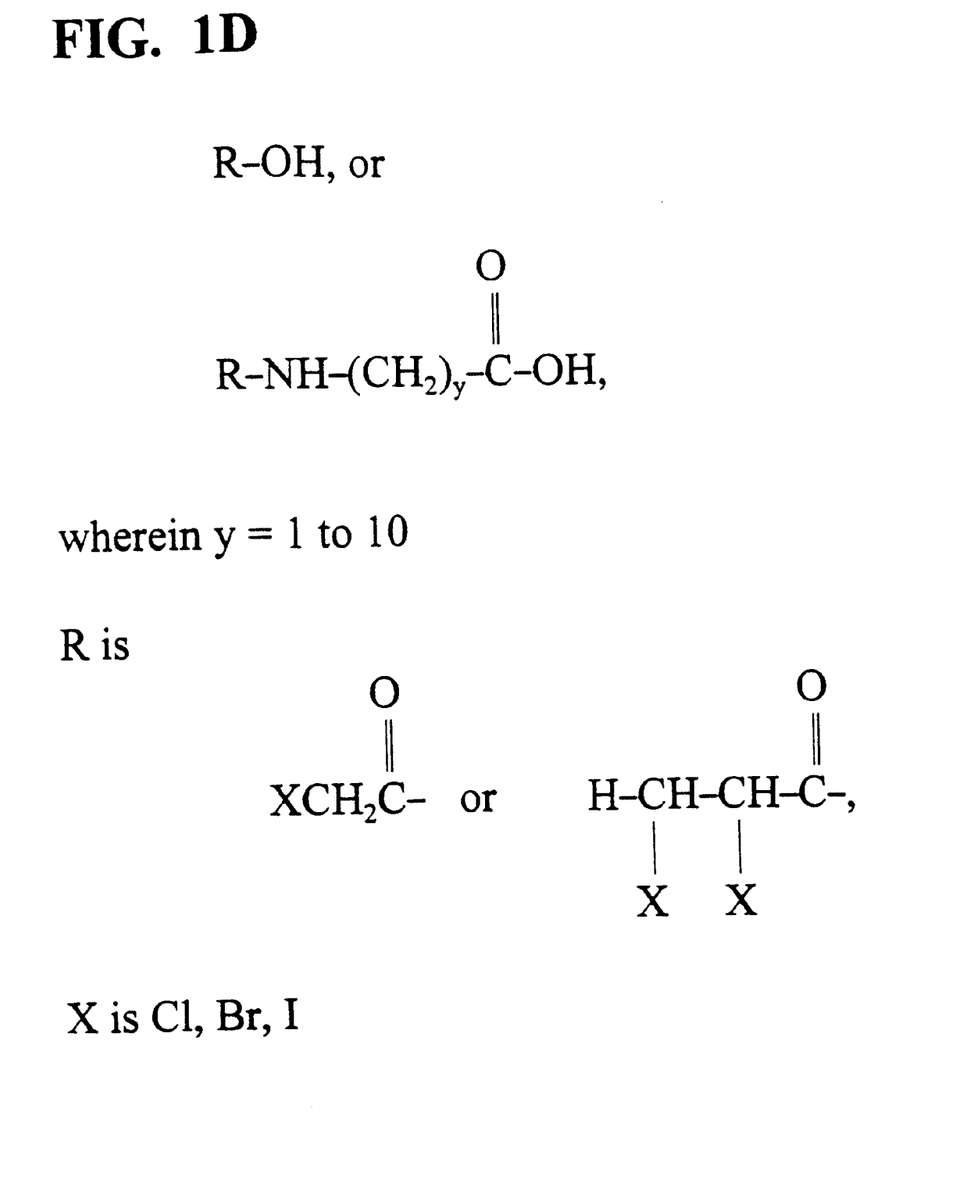
FIG. 1D illustrates haloacyl acid reagents that can be used in the method according to the invention.

To further illustrate examples of possible haloacyl reagents for use in the process of the invention, attention is invited to FIGS. 1A to 1D. For example, the reagent can be an active ester, as shown in FIG. 1A. Active esters of N-hydroxysuccinimide are particularly preferred. Additionally, the reagent can be an anhydride material, as illustrated in FIG. 1B. The haloacyl reagent also can be a haloacyl chloride, the general formulae for which are shown in FIG. 1C. An additional possible reagent includes acids of the haloacyl compounds. The formulae for such reagents are illustrated in FIG. 1D.

As shown in FIGS. 1A to 1D, the haloacyl reagent can include a single halogen substituent (e.g., a haloacetyl compound) or two halogen substituents (e.g., an $\alpha,\beta$ dihaloacyl compound). An example of a haloacyl reagent containing halo groups in an $\alpha,\beta$ configuration is SDBP (available from Pierce Chemical Co.). This reagent has been reported to react with amines to form an aziridine linkage, however, no proof of this linkage has been demonstrated for macromolecular conjugates. In the experience of the applicant, low molecular weight amine compounds, but not macromolecular species (e.g., proteins), react readily with the dibromoacyl group on polysaccharides. As seen in the examples which follow, conjugate yields are relatively low at room temperature, but are significantly enhanced by raising the reaction temperature to about 42° C. However, even conjugates produced at lower temperatures, with relatively low ratios of protein to polysaccharide, can be immunogenic. Thus, these conjugate products are useful as vaccines and immunogens according to the invention.

In certain examples, proteins are coupled to high molecular weight (>about 100 kDa) haloacyl functionalized polysaccharides. Since it is generally easier to conjugate lower molecular weight species (e.g., proteins, peptides, or haptens having a molecular weight lower than about 100 kDa), it would be expected that lower molecular weight polysaccharides, oligosaccharides, and other carbohydrates would be even easier to conjugate using the described chemistry.

Although applicant does not wish to be bound by any particular chemical theories or reaction mechanisms, the following information is given as additional background information relating to the invention. It is believed that lysines, which are typically found on the outside of proteins, are the principal amino acid nucleophile on the protein that reacts with the haloacyl group on the functionalized polysaccharide. The $\epsilon$-amines of lysines have a pKa in the range of 9–10, which is consistent with the finding that a pH in this range, where the lysine amine would be deprotonated, led to good conjugate yields. If histidine (with a pKa of about 6) or either methionine or cysteine (amino acids with a thiol) were involved, good coupling would be expected at much lower pH. Furthermore, it should be noted that the tetanus toxoid used had no detectable free thiols, so thio-ether linkages are not forming. In work done by the applicant., it was shown that a test protein (BSA) containing about 0.5 mole thiol/mole protein would couple at neutral pH, but if the thiols were blocked, a more alkaline pH and elevated temperature was necessary for good conjugation.

The elevated temperature may serve to increase the reactivity of nucleophiles on the protein with the haloacyl group. It also may serve to slightly "loosen" the protein structure, thereby increasing flexibility and enhancing access to reactive groups on the protein.

The invention will be described in more detail below in terms of various specific examples. These specific examples should be construed as illustrating the invention, and not as limiting the same.

EXAMPLE 1

In this example, a conjugate of tetanus toxoid and Pn14 was prepared using N-succinimidyl-2,3-dibromopropionate ("SDBP") as the haloacyl activating reagent to functionalize the polysaceharide.

As a first step in the process, a Pn14 polysaceharide was derivatized with amines. To do so, Pn14, obtained from the American Tissue Culture Collection, was functionalized with amines in the general manner described by Lees, et al., Vaccine, Vol. 14, No.3 (1996), pp. 190–198. Initially, 20 mg of Pn14 was solubilized overnight in 2 ml of water. Then, 60 µl of CDAP, obtained from Research Organics, at 100 mg/ml in acetonitrile was added. Thirty seconds later, 180 µl of 0.2 M triethylamine was added. At 2.5 min, 1 ml of a solution containing 0.5 M hexanediamine in 0.75 M HEPES (N-hydroxyethyl piperazine N'-2-ethanesulfonicacid) and 5 mM ethylenediamine tetraacetate ("EDTA") (providing a mixture having a pH of about 7.3) was added to the CDAP/polysaccharide mixture. After an overnight reaction at 4° C., the sample was exhaustively dialyzed into saline. The presence of free amines was determined using the trinitrobenzenesulfonic acid (TNBS) assay as described by Vidal et al., J. Immunol. Meth., Vol. 86 (1986), beginning at page 155 (which article is entirely incorporated herein by reference). The presence of Pn14 was determined using the assay method of Monsigny et al. (Anal. Chem., Vol. 175 (1988), beginning at page 525 (which article also is entirely incorporated herein by reference), using Pn14 as the standard. It was determined that the resulting derivatized polysaccharide contained a ratio of 17.3 amines per 100 kDa Pn14.

As the next step, the amine derivatized Pn14 was functionalized with haloacyl groups to produce a Pn14 labeled with 2,3 dibromopropionate. 50 µl of a mixture of 0.75 M HEPES and 5 mM EDTA (pH 7.3) was added to 2 mg of the above produced $NH_2$-Pn14 material in 0.53 ml saline, on ice. 1.5 mg of SDBP (available from Pierce Chemical) in 50 µl of dimethylformamide ("DMF") was added while mixing. After one hour, the sample was desalted on two P6 cartridges (available from BioRad) in series, equilibrated with 10 mM sodium acetate, 0.1 M NaCl, and 2 mM EDTA (pH 5), and concentrated with a Centricon 50 device (available from Amicon) to about 400 µl. This procedure produced the labeled Pn14 polysaccharide.

The haloacyl labeled Pn14 polysaccharide was then coupled to unmodified tetanus toxoid protein. In this procedure, 2.2 mg of tetanus toxoid (obtained from SmithKline Beecham of Rixensart, Belgium) in 140 µl of phosphate buffered saline ("PBS") were added to the dibromopropionate-Pn14, followed by the addition of 75 µl of 0.1 M sodium borate (pH 9.3). The solution was incubated for 30 min at 37° C. and then overnight at room temperature, in the dark. The mixture was passed over a 1×50 cm S400HR gel filtration column (available from Pharmiacia), equilibrated with PBS. The void volume fractions were pooled and concentrated using a Macrosep 50 device (available from Filtron Corporation) and filtered through a Millex HV filter.

The protein content of the resulting reaction mixture was determined using the BioRad assay with tetanus toxoid as the standard. The amount of Pn14 was determined using the assay method of Monsigny et al., as described above, with Pn14 as the standard. It was determined that the resulting protein-polysaccharide conjugate product contained 66 µg/ml tetanus toxoid and 0.71 mg/ml Pn14.

This conjugate material was used to immunize mice to determine whether immune responses to the protein and polysaccharide were induced. Groups of three Balb/C mice were pre-bled and injected i.p. with 33 or 10 µl of the conjugate, in a volume of 100 µl saline. Mice in another group were injected with saline alone as a control. The mice were bled on day 28, and boosted with 10.8 µg Pn14, as the conjugate (1 µg TT and 10.8 µg Pn14). The mice were again bled 14 days later. The sera collected at day 42 were tested in an ELISA assay as follows. Nunc Maxisorb ELISA plates were coated with Pn14 or tetanus toxoid at 1 µg/ml in PBS. Bound antisera, at a 1:1000 dilution, were measured using gamma-specific rabbit anti-mouse IgG conjugated with horseradish peroxidase at a 1:4000 dilution in PBS/Tween. TMB was used as the substrate. The color reaction was quenched at 15 minutes. The ELISA absorbance readings were taken at 430 nm.

The following Table illustrates the immunogenicity data obtained from the sera collected at day 42.

TABLE 1

Sera was assayed at a 1:1000 dilution for total IgG binding to Pn14 and tetanus toxoid using ELISA

| Dose | anti-Pn14* | anti-TT* |
|---|---|---|
| 33 µl | 1.431 | 1.844 |
| 10 µl | 0.923 | 1.021 |
| saline | 0.297 | 0.260 |

*ELISA absorbance readings taken at 430 nm

As is evident from Table 1, the anti-Pn14 and anti-TT titers were markedly higher for the conjugate samples as compared to the saline control sample.

EXAMPLE 2

In this example, tetanus toxoid was conjugated to a Vi antigen polysaccharide. First, an amine derivatized Vi polysaccharide was prepared. 3.4 ml of Vi antigen solution (at a concentration of 5 mg Vi/ml, obtained from SmithKline Beecham) was mixed in 340 µl of 1 M 2-(N-morpholino) ethanesulfornic acid ("MES") (pH 6). Then, 68 µl of 0.1 M sulfo-N-hydroxysuccinimide and 90.4 mg ethylenediamine-2HCl were added. Solid 1-(3-dimethylaminopropyl)-3-ethylcarbodiimide ("EDC") was added to the reaction mixture until the mixture had a concentration of 10 mg EDC/ml. The reaction was allowed to proceed for four hours at room temperature, and then the product was dialyzed exhaustively into saline and azide. It was determined that the reaction product had 15.9 $NH_2$/100 kDa of Vi.

This amine derivatized Vi material was then iodoacetylated. 1.4 ml of the $NH_2$-Vi (at a concentration of 3.6 mg/ml) was added to 100 µl of a mixture of 0.75 M HEPES and 0.5 mM EDTA (pH=7.3), and 32 µl 0.1 M N-succinimidyl iodoacetate ("SIA," available from BioAffinity Systems). After about two hours, the polysaecharide was washed by diluting, to 10 ml and then concentrated to about 200 µl with a pressure ultrafiltration device with a 30 K membrane (membrane available from Filtron Omega). The sample was removed and the membrane washed with 0.1 M sodium borate (pH 9.3). The final volume was 760 µl.

At this time, the haloacyl derivatized Vi polysaccharide was conjugated to an unmodified tetanus toxoid protein. 300 µl of tetanus toxoid (containing 5 mg tetanus toxoid) in saline was added to the polysaccharide solution, and the resulting mixture was incubated in the dark at 46° C. for about 22 hours. The reaction was quenched by adding 20 µl of 10 mM mercaptoethanol and allowed to stand for one hour. 0.75 ml of the reaction product was run on a 1×45 cm S400HR column, and the high molecular weight fractions were pooled. The remaining material was dialyzed into PBS.

All material was sterile filtered with a Millex GV device. It was determined that the high molecular weight fraction, Fraction H, contained 0.71 mg TT/mg Vi. This Fraction H was used in an immunogenicity study on mice. Groups of four Balb/c mice were immunized s.c. with 5 µg of Vi, either alone or as a conjugate. The mice were given booster immunizations on day 14 and bled about 14 days later. The collected sera were tested in an ELISA assay. Nunc Maxisorb ELISA plates were coated overnight with Vi antigen at 1 µg/ml in sodium carbonate buffer at pH 9. Antisera were tested at various dilutions to determine titer with a 0.1 OD cutoff.

The following anti-Vi titer data was obtained:

TABLE 2

| Immunogen | Anti-Vi Titer |
|---|---|
| TT-SIA-Vi | 1086 |
| Vi | 119 |

From this Table, it can be readily seen that the anti-Vi titer is higher for the conjugate produced by the process of the invention (i.e., the TT-SIA-VI conjugate), as compared to Vi antigen injected alone.

EXAMPLE 3

In this Example, a tetanus toxoid-Neisseria PsC conjugate was produced using SDBP as the haloacylating reagent. Neisseria PsC (obtained from SmithKline Beecham) was solubilized overnight in water to a concentration of 10 mg/ml. 1 ml of 1 M MES (pH 6) was added to 5.5 ml of the PsC, and then, 307 mg hexanediamine-2HCl was added to this mixture. Thereafter, 7 mg sulfo-N-hydroxysuccinimide also was added to the mixture. The pH of the resulting reaction mixture was measured at 5.75.

Then, 500 µl of 0.5 M EDC was added. After an overnight reaction at room temperature, the solution was dialyzed into saline, followed by diafiltration on a YM30 membrane (available from Amicon) and desalting on a 2.5×12 cm P6DG column (available from BioRad). The product ($NH_2$-PsC) was concentrated to 6.1 ml and assayed for free amines (by the method of Vidal et al., supra.) and PsC (by the method of Monsigny et al., supra.), with PsC as the standard. It was determined that the resulting $NH_2$-PsC material had a ratio of 7.5 amines per 100 kDa of the polysaccharide.

This $NH_2$-PsC material was then haloacylated. 100 µl of a mixture of 0.75 M HEPES and 5 mM EDTA was added to 1 ml of the $NH_2$-PsC material (9.8 mg $NH_2$-PsC), and 100 µl 0.1 M SDBP (in DMF) was added. After two hours at 4° C., the solution was desalted on a 1.5×15 cm P6DG column (available from BioRad), and the void volume fractions were pooled and concentrated to 350 µl using a Centricon 50 device (available from Amicon.). The PsC concentration was determined to be 18.2 mg/ml.

112 µl of the derivatized polysaccharide (2 mg) was pipetted into micro fuge tubes, and 1 or 2 mg of tetanus toxoid (obtained from SmithKline Beecham) at 16.8 mg/ml in saline was added. At time zero, 50 µl 0.1 M sodium borate (pH 9.3) or potassium borate (pH 10) was added. The samples were split and incubated at room temperature or 42° C. and assayed at the indicated times by HPLC. The amount of conjugate produced is assumed to correspond to the void volume absorbance of the high molecular weight peak. The percent conjugate is calculated as the percent of the UV absorbance for the conjugated protein peak, based on the total UV absorbance of the protein, as measured by the HPLC.

All samples were then incubated an additional 24 hours at 42° C. and again assayed by HPLC. Groups A2, B1, and B2 were pooled and quenched by the addition of 25 µl of 10 mM mercaptoethanol for 15 minutes. Groups A1, C1, and C2 were pooled and quenched by the addition of 25 µl of 10 mM mercaptoethanol for 15 minutes. Each pool was passed over a S400HR gel filtration column (available from Pharmacia), equilibrated with PBS, sterile filtered, and assayed for tetanus toxoid and PsC.

The HPLC test results are shown in the following Table:

TABLE 3

At about 18 hours, 35 hours, and 60 hours, 5 μl aliquots were assayed by HPLC size exclusion chromatography on a Beckman SEC G4000 column, 0.1M KPO4, pH 7.3, run at 1 ml/min. The flow was monitored by UV absorbance.

| Sample | PsC-DBP | TT   | pH  | Temp    | 18 hr  | 35 hr | 60 hr |
|--------|---------|------|-----|---------|--------|-------|-------|
| A1     | 2 mg    | 2 mg | 9.3 | RT[1]   | 6%[2]  | 10%   |       |
| A2     | 2 mg    | 2 mg | 9.3 | 42° C.  | 19%    | 30%   | 44%   |
| B1     | 2 mg    | 2 mg | 10  | RT      | 8%     | 14%   |       |
| B2     | 2 mg    | 2 mg | 10  | 42° C.  | 28%    | 41%   | 49%   |
| C1     | 2 mg    | 2 mg | 9.3 | RT      | 9%     | 13%   |       |
| C2     | 2 mg    | 1 mg | 9.3 | 42° C.  | 29%    | 45%   | 56%   |

[1]"RT" stands for room temperature
[2]The percentages represent percentage of protein conjugated.

From this data, the following observations can be made: (1) under all conditions, coupling was significantly enhanced by increasing the temperature and pH; (2) even extended reaction times (up to 35 hours) at room temperature were not as efficient at promoting coupling as the elevated temperature; (3) coupling efficiency is higher at a lower protein:Ps ratio (0.5 vs 1 mg TT/mg Ps); and (4) very good yields can be obtained at pH 9.3.

The ability to use the chemistry according to the invention to prepare low ratio conjugates with good coupling efficiency is illustrated in Samples A2 and C2 in which 1.0 or 0.5 mg TT/mg PsC is used, respectively. It is seen that the coupling efficiency is higher at the lower ratio of Sample C2 (44% vs 56%), respectively. The estimated protein to PsC ratios in the resulting conjugates are 0.44 mg/mg and 0.28 mg/mg, respectively. Therefore, in Sample C2, less protein is needed to prepare conjugate while good coupling yields are still obtained.

EXAMPLE 4

In this Example, tetanus toxoid protein was coupled to a Neisseria PsC polysaccharide using SIA as the polysaccharide functionalizing reagent.

First, NH$_2$-PsC was prepared in the same manner as described in Example 3. One ml of the NH$_2$-PsC material (at a concentration of 9.8 mg/ml) was mixed with 100 μl of a mixture of 0.75 M HEPES and 0.5 mM EDTA (pH=7.3) and with 100 μl 0.1 M SIA in DMF. After about two hours, the reaction mixture was desalted on a P6DG column (available from Pharmacia), equilibrated with 10 mM sodium acetate and 2 mM EDTA (pH 5). The fractions containing the polysaceharide peak were pooled and concentrated using a Centricon 50 device (available from Amicon), and the resulting Neisseria PsC concentration was determined to be about 10 mg/ml.

400 μl of the SIA-PsC material prepared above was added to 240 μl of a tetanus toxoid solution at a concentration of 16.8 mg/ml in saline, and 100 μl of 0.1 M sodium borate (pH 10) was added. The sample was incubated in the dark for 40 hours at 42° C., quenched by the addition of 25 μl 10 mM mercaptoethanol for 30 minutes and fractionated on a 1×50 cm S400HR column equilibrated with saline. The high molecular weight fractions were pooled, sterile filtered, and assayed for protein and polysaceharide. The ratio was determined to be 0.28 mg TT/mg PsC.

EXAMPLE 5

Immunogenicity data from the conjugates of Examples 3 and 4 were obtained. From Example 3, Samples A1, C1, and C2 were pooled and fractionated, and this material constituted Sample 5A for this Example. The conjugate prepared in Example 4 was used as Sample 5B. In this manner, conjugates produced using SDBP as a haloacyl functionalizing reagent (Sample 5A) can be compared with conjugates produced using SIA (Sample 5B).

Groups of four mice Balb/c were immunized with 10 μg of Neisseria PsC, either alone (as a control sample) or conjugated (Samples 5A and 5B). The mice were boosted with the same antigen on day 14 and bled 14 days later. Sera were assayed for antibodies against Neisseria PsC. The ability to protect was determined using a bactericidal assay. The following test results were obtained:

TABLE 4

| Immunogen          | Anti-PsC Titer | Bactericidal titer* |
|--------------------|----------------|---------------------|
| Sample 5A          | 3019           | 1:320               |
| Sample 5B          | 4771           | 1:320               |
| Reference antisera |                | 1:640               |
| PsC alone          |                | less than 1:10      |

*Performed as described by Wong, K.H., et al., Journal of Biological Standards, Vol. 5 (1977), beginning at page 197, which article is entirely incorporated herein by reference.

From this data, it is evident that the conjugates produced according to the invention provided excellent antibody responses, including highly functional antibody responses which were bactericidal, e.g., protective.

EXAMPLE 6

In this Example, an oligosaccharide is functionalized with a pendant haloacyl group and coupled to a protein via this group, which is located at an end of the oligosaccharide. Generally, the hydrolysis and derivatization with amines, as described below, is accomplished according to the method described in Porro, U.S. Pat. No. 5,153,312, which patent is entirely incorporated herein by reference.

Pneumococcal type 14 polysaccharide ("Pn14") is solubilized at 5 mg/ml in 0.5 M aqueous trifluoroacetic acid in a sealed ampule and heated at 70° C. for three hours. After neutralization, the oligosaccharides are fractionated on a Sephadex G25 column, equilibrated with 0.15 M NaCl. The carbohydrate concentration is determined using the method of Monsigny (described above), and the number of reducing ends is determined using bicinchoninic acid (available from Pierce Chemical), using galactose as the standard. The ratio of reducing ends to total carbohydrate allows the molecular weight of the oligosaccharides to be estimated. Oligosaccharides with a molecular weight of about 3000 to 5000 daltons are selected for this example.

Ethylenediamine is coupled to the reducing end of the oligosaccharide using reductive amination. The oligosaccharide solutions are made 0.5 M in ethylenediamine at pH 5, and then solid sodium cyanoborohydride is added to a final concentration of 50 mM. After 2 days in the dark at room temperature, the amine-labeled oligosaccharides are desalted on a Sephadex G10 column, equilibrated with 20 mM NaCl. The resulting material is concentrated by perevaporation, in the dark, to 25 mg/ml carbohydrate. The ratio of amines to carbohydrate is determined using TNBS to measure the amines.

The amine-derivatized oligosaecharide is then iodoacetylated. A mixture of 0.75 M HEPES and 0.5 mM EDTA is added to the NH$_2$-oligosaccharide until the resulting solution is 0.1 M in HEPES and the pH is adjusted to 7.3. A ten-fold molar excess of SIA to amines is added from a 0.1 M stock SIA solution (in DMF), and the reaction is allowed to proceed for two hours in the dark. The sample is again desaited using a Sephadex G10 column and perevaporated in the dark to a final concentration of 25 mg/ml.

The iodoacetylated oligosaccharide is then combined with tetanus toxoid such that there is an equal weight of each component and the final concentration of each is about 10 mg/ml. The mixture is incubated in the dark at 43° C., and the extent of conjugation is monitored by size exclusion HPLC using a refractive index ("RI") and UV detector. The increase in the RI signal for the protein peak, as well as an increase in the molecular weight, indicates coupling of the carbohydrate. It is expected that sufficient conjugation would occur in about 24 hours. The unconjugated oligosaccharide is removed from the conjugate by gel filtration on a SI OOHR column (available from Pharmacia).

The conjugate material (an oligosaccharide-protein conjugate) can be used for immunization to induce an immune response in a subject.

OTHER FEATURES OF THE INVENTION

This invention further relates to vaccines and immunogens that can be prepared from the conjugates produced in accordance with the invention. In a vaccine or immunogen, the conjugates produced according to the invention can be combined with a pharmaceutically acceptable carrier or delivery vehicle by conventional techniques known to those skilled in the art. Such products will contain an effective amount of the conjugate according to the invention, together with a suitable amount of vehicle, so as to provide the form for proper administration to a subject or other intended use. Vaccines may include alum or other adjuvants.

Exemplary pharmaceutically acceptable carriers or vehicles include, for example, sterile liquids, such as water and oils, including those of petroleum, animal, vegetable, or synthetic origin, such as peanut oil, soybean oil, mineral oil, sesame oil, and the like. Saline is a preferred vehicle when the pharmaceutical composition is administered intravenously. Aqueous dextrose and glycerol solutions also can be employed as liquid vehicles, particularly for injectable solutions. Suitable pharmaceutical vehicles are well known in the art, such as those described in E. W. Martin, *Remington's Pharmaceutical Sciences*, which source is entirely incorporated herein by reference.

The invention also relates to the method for treating a subject and inducing an immune response by administering an immunostimulatory amount of the vaccine according to the invention. The conjugates according to the invention may be administered to any subject for which the treatment may be beneficial, including mammals, especially humans, horses, cows, pigs, sheep, deer, dogs, and cats, as well as other animals, such as chickens. An "immunostimulatory amount" refers to that amount of vaccine that is able to stimulate the immune response of the subject for prevention, amelioration, diagnosis, or treatment of diseases. The vaccines of the invention may be administered by any suitable route, but they preferably are administered by intravenous, intramuscular, intranasal, or subcutaneous injection.

In addition, the vaccines or immunogens in accordance with the invention can be administered for any suitable purpose, such as for therapeutic, prophylactic, or diagnostic purposes.

In describing the invention, applicant has set forth certain theories in an effort to disclose how or why the invention works in the manner in which it works. These theories are set forth for informational purposes only. Applicant is not to be bound by any specific chemical or physical mechanisms or theories of operation.

Additionally, applicant has described several examples and processes for producing conjugates in accordance with the invention. While these procedures may be further optimized (e.g., optimizing the pH conditions during coupling, reaction times, reaction temperatures, etc.), such optimization of the process and reaction conditions is a matter of routine experimentation.

While the invention has been described in terms of various preferred embodiments and specific examples, those skilled in the art will recognize that various changes and modifications can be made without departing from the spirit and scope of the invention, as defined in the appended claims.

I claim:

1. A method for preparing an immunogenic conjugate, comprising:
    functionalizing a first moiety selected from the group consisting of polysaccharides, oligosaccharides, and other carbohydrates with one or more pendant haloacyl groups;
    reacting the functionalized first moiety with a second moiety selected from the group consisting of proteins, peptides, and lipoproteins having amine groups to form a conjugate having a covalent linkage between one or more haloacyl groups on the first moiety and an amine group on the second moiety, wherein the first moiety is a Pneumococcal polysaccharide, Vi antigen, or a *Neisseria meningiditis* polysaccharide type C.

2. A method according to claim 1, wherein the first moiety is a polysaccharide.

3. A method according to claim 1, wherein the functionalizing procedure includes reacting the first moiety with N-succinimidyl iodoacetate.

4. A method according to claim 1 wherein the second moiety is a protein.

5. A method according to claim 4, wherein the protein is a tetanus toxoid.

6. A method according to claim 5, wherein the first moiety is a Pneumococcal type 14 polysaccharide.

7. A method according to claim 5, wherein the first moiety is Vi antigen.

8. A method according to claim 5, wherein the first moiety is *Neisseria meningiditis* polysaccharide type C.

9. A method according to claim 1, wherein the functionalizing procedure is accomplished by reacting the first moiety with a haloacyl containing reagent.

10. A method according to claim 9, wherein the haloacyl containing reagent is a member selected from the group consisting of active esters of haloacyl compounds, anhydrides of haloacyl compounds, haloacyl chlorides, haloacyl acid compounds, active esters of $\alpha,\beta$ dihaloacyl compounds, anhydrides of $\alpha,\beta$ dihaloacyl compounds, $\alpha,\beta$ dihaloacyl chlorides, and $\alpha,\beta$ dihaloacyl acid compounds.

11. A method according to claim 9, wherein the haloacyl containing reagent is a haloacetyl containing reagent.

12. A method according to claim 1, wherein the functionalizing procedure includes reacting the first moiety with N-succinimidyl-2,3-dibromopropionate.

13. A conjugate produced by the process of claim 1.

14. A protein-polysaccharide conjugate produced by the process of claim 2.

15. An immunogenic composition comprising the conjugate of claim 1 and a pharmaceutically acceptable carrier or delivery vehicle.

16. An immunogenic composition comprising the conjugate of claim 2 and a pharmaceutically acceptable carrier or delivery vehicle.

17. A method of inducing an immune response in a subject, comprising: administering an immunogenic composition according to claim 15 to the subject.

18. A method of inducing an immune response in a subject, comprising: administering an immunogenic composition according to claim 16 to the subject.

* * * * *

UNITED STATES PATENT AND TRADEMARK OFFICE
CERTIFICATE OF CORRECTION

PATENT NO.: 6,087,328
DATED: July 11, 2000
INVENTOR: Andrew Lees

It is certified that an error appears in the above-identified patent and that said Letters Patent is hereby corrected as shown below:

On the Title Page, Item [57], in the Abstract, line 16, "Furthermnore" should read --Furthermore--.

Signed and Sealed this

Twenty-ninth Day of May, 2001

Attest:

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

PATENT NO. : 6,087,328
DATED : July 11, 2000
INVENTOR(S) : Andrew Lees

It is certified that error appears in the above-identified patent and that said Letters Patent is hereby corrected as shown below:

<u>Title page,</u>
Item [57], ABSTRACT,
Line 16, "Furthermnore" should read -- Furthermore --.

Signed and Sealed this

Ninth Day of November, 2004

JON W. DUDAS
*Director of the United States Patent and Trademark Office*